(12) United States Patent
Copeland et al.

(10) Patent No.: US 11,286,450 B2
(45) Date of Patent: Mar. 29, 2022

(54) CULTURE SYSTEM FOR GROWING MICROORGANISMS

(71) Applicant: Oxyrase, Inc., Mansfield, OH (US)

(72) Inventors: James C. Copeland, Mansfield, OH (US); John E. Richey, Mansfield, OH (US)

(73) Assignee: Oxyrase, Inc., Mansfield, OH (US)

( * ) Notice: Subject to any disclaimer, the term of this patent is extended or adjusted under 35 U.S.C. 154(b) by 327 days.

(21) Appl. No.: 16/555,059

(22) Filed: Aug. 29, 2019

(65) Prior Publication Data

US 2020/0080040 A1   Mar. 12, 2020

Related U.S. Application Data

(60) Provisional application No. 62/730,101, filed on Sep. 12, 2018.

(51) Int. Cl.
*C12M 1/22* (2006.01)
*C12M 1/32* (2006.01)
*C12M 1/00* (2006.01)

(52) U.S. Cl.
CPC ............ *C12M 23/12* (2013.01); *C12M 23/10* (2013.01); *C12M 23/34* (2013.01)

(58) Field of Classification Search
CPC ...... C12M 23/12; C12M 23/10; C12M 23/34; C12M 23/38; B01L 2200/0689; B01L 2300/042; B01L 2300/0848; B01L 3/508; B01L 3/06

USPC .......................................... 435/289.1, 305.3
See application file for complete search history.

(56) References Cited

U.S. PATENT DOCUMENTS 3,158,553 A      11/1964  Carski
9,284,522 B2 *   3/2016   Huet ....................... C12M 23/46
2002/0045245 A1  4/2002   Copeland et al.

FOREIGN PATENT DOCUMENTS

EP     0 066 199 A2   12/1982
EP     0 171 174 A2    2/1986
JP     2015 226532 A  12/2015

OTHER PUBLICATIONS

International Search Report for PCT Application No. PCT/US2019/048750 dated Nov. 6, 2019.

* cited by examiner

*Primary Examiner* — Liban M Hassan
(74) *Attorney, Agent, or Firm* — Fay Sharpe LLP (57) ABSTRACT

A culture system includes a dish and a lid. The dish comprises a base, a sidewall extending from the base, and a track extending outwardly from an outer surface of the sidewall. The lid comprises a central horizontal wall and a recess formed by two sidewalls and a top wall. At least one key extends downwardly from the recess. The sidewall of the dish extends into the recess of the lid, and the key engages the track. The track is shaped so that the lid rises or falls relative to the base of the dish when the lid is rotated relative to the dish.

20 Claims, 8 Drawing Sheets

CULTURE SYSTEM FOR GROWING MICROORGANISMS

CROSS-REFERENCE TO RELATED APPLICATIONS

This application claims priority to U.S. Provisional Patent Application Ser. No. 62/730,101, filed on Sep. 2, 2018, which is incorporated by reference in its entirety.

BACKGROUND

The present disclosure relates to culture systems and method for growing microorganisms (e.g., anaerobic microorganisms). The culture system includes a dish and a lid, which can be sealed to produce an anaerobic environment therein. An oxygen reducing agent, such as a biocatalytic oxygen reducing agent, may be incorporated into the media present in the culture system. This creates an environment suitable for growing and maintaining anaerobe microorganisms. The dish and the lid are designed to be rotated so as to easily create or break the seal.

Microorganisms can be divided into groups based on their need for, and tolerance of, oxygen. Those that require oxygen to grow are "aerobes". Some microorganisms are able to grow with or without oxygen. These are "facultative anaerobes". Another group of microorganisms can grow only in the presence of very low levels of oxygen. These are the "microaerophiles". Finally, "anaerobes" cannot tolerate oxygen and are either inhibited by or killed by the presence of oxygen.

Microorganisms can be grown and studied by plating in a Petri dish. This is a round, shallow, flat-bottomed, glass or plastic dish (often e.g. 10 cm diameter) that cooperates with a lid. The dish is filled with a solid cell culture medium that provides a necessary and selective environment for a specific microorganism. Solid medium in a Petri dish can be prepared by pouring sterile molten or liquid (agar- or gelatin-based) medium into the dish to a depth of 3-5 mm and allowing it to set. Generally, freshly poured plates should be left with the lid partly off so that the surface moisture can evaporate.

Working with microbes that are microaerophiles or anaerobes poses a problem. These microbes must be grown in a controlled gaseous environment that lacks oxygen, or at least most of the oxygen, found in air. This can be done by sealing the culture dish to separate the microbes from the outside atmosphere.

Some issues arise in using sealed culture dishes. First, as the cell culture medium is poured and solidifies, the moisture needs to evaporate, but the medium must also be protected from the ambient environment so that it is not contaminated. As a result, water accumulates in the headspace of a sealed dish. Second, it can be difficult to break the seal on the culture dish and open the culture dish. It would be desirable to address these aspects.

BRIEF DESCRIPTION

The present disclosure relates to culture systems and apparatuses which can be used to cultivate microorganisms in a low-oxygen environment. The systems comprise a dish and a lid. The dish includes a track, and the lid includes at least one key. The key interacts with the track such that the dish and lid form a seal when rotated relative to each other in one circumferential direction, and the seal is broken when the dish and lid are rotated in the other circumferential direction.

Disclosed in various embodiments herein are apparatuses for cultivating anaerobe microorganisms, comprising a dish and a lid. The dish comprises a base, a sidewall extending upwards from the base to define a cavity, and a track extending outwards from an outer surface of the sidewall. The track comprises at least one track portion, and usually a plurality of track portions. Each track portion includes a lower landing with a stop at a terminal end, a ramp extending from the lower landing to an upper landing, and a stop at a terminal end of the upper landing. The lid comprises a central horizontal wall, a downward-facing recess, and at least one key extending downwards from a top wall of the recess. The at least one key cooperates with the at least one track portion so that (A) the lid rises relative to the base of the dish when the lid is rotated in a first circumferential direction, and (B) the lid falls relative to the base of the dish when the lid is rotated in an opposite circumferential direction.

The at least one track portion may further comprise a bump between the ramp and the upper landing. In particular embodiments, the track has a total of four track portions evenly spaced about a circumference of the dish, and the lid has a total of four keys evenly spaced about a circumference of the lid. More generally, the number of track portions on the track is equal to the number of keys on the lid. In such embodiments, the lower landing stop and the upper landing stop of adjacent track portions can be provided by a common wall.

The central horizontal wall of the dish may be joined to the downward-facing recess by a seal ring. The downward-facing recess may be formed by an outer sidewall and an inner sidewall joined together at one end by the top wall.

The upper landing and the lower landing of the at least one track portion should be separated by a height such that when an associated culture media having a surface is formed in the dish, (A) the seal ring does not contact the culture media surface when the at least one key engages the upper landing of the at least one track portion; and (B) the seal ring contacts the culture media surface when the at least one key engages the lower landing of the at least one track portion.

Generally, the outer sidewall is taller than the inner sidewall of the lid. This permits the key(s) to engage the track.

In some embodiments, the lid further comprises strengthening ribs spaced about a circumference of the lid and extending radially outward from the outer sidewall. The lid can also further comprise a stacking ring extending upwards from an upper edge of the lid.

The dish may further comprise a lip on an inner surface of the sidewall. The base of the dish may also include pores.

Also disclosed herein are methods of cultivating and enumerating anaerobes, microaerophiles, or facultative anaerobe microorganisms, comprising: providing a culture apparatus comprising a dish and a lid as described above; placing a solidified culture medium in the dish; and covering the dish containing the solidified culture medium with the lid such that the at least one key engages the lower landing of the at least one track portion, thereby forming a sealed headspace between the culture medium and the lid.

The culture dish can be unsealed by circumferentially rotating the lid relative to the dish. The solidified culture medium may comprise an oxygen reducing agent that removes oxygen from the headspace and the culture medium.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the apparatuses and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language such as "about" may be applied to modify any quantitative representation that may vary without resulting in a change in the basic function to which it is related. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation. The terms "top" and "bottom" or "base" are also relative to each other, as are the terms "upward" and "downward". The culture apparatuses described herein can be inverted, so that such relative terms are appropriate.

The terms "horizontal" and "vertical" are used to indicate direction relative to an absolute reference, i.e. ground level. However, these terms should not be construed to require structures to be absolutely parallel or absolutely perpendicular to each other.

The present disclosure relates to a culture system or apparatus or plate that includes two components, a dish and a lid. The lid includes a sealing ring that engages a culture medium surface in the dish when the apparatus is inverted to form a media-ring seal. The seal traps gas in the headspace between the media surface and the inside of the lid. A biocatalytic oxygen reducing agent may be incorporated into the culture medium, which reacts with oxygen in the media and the headspace to create an environment suitable for growing anaerobe microorganisms. The combination of a track on the dish and a key system on the lid allows the plate to be unsealed and opened with less effort, thereby reducing the likelihood of damaging the culture system, and enhancing automation.

Figure 1:
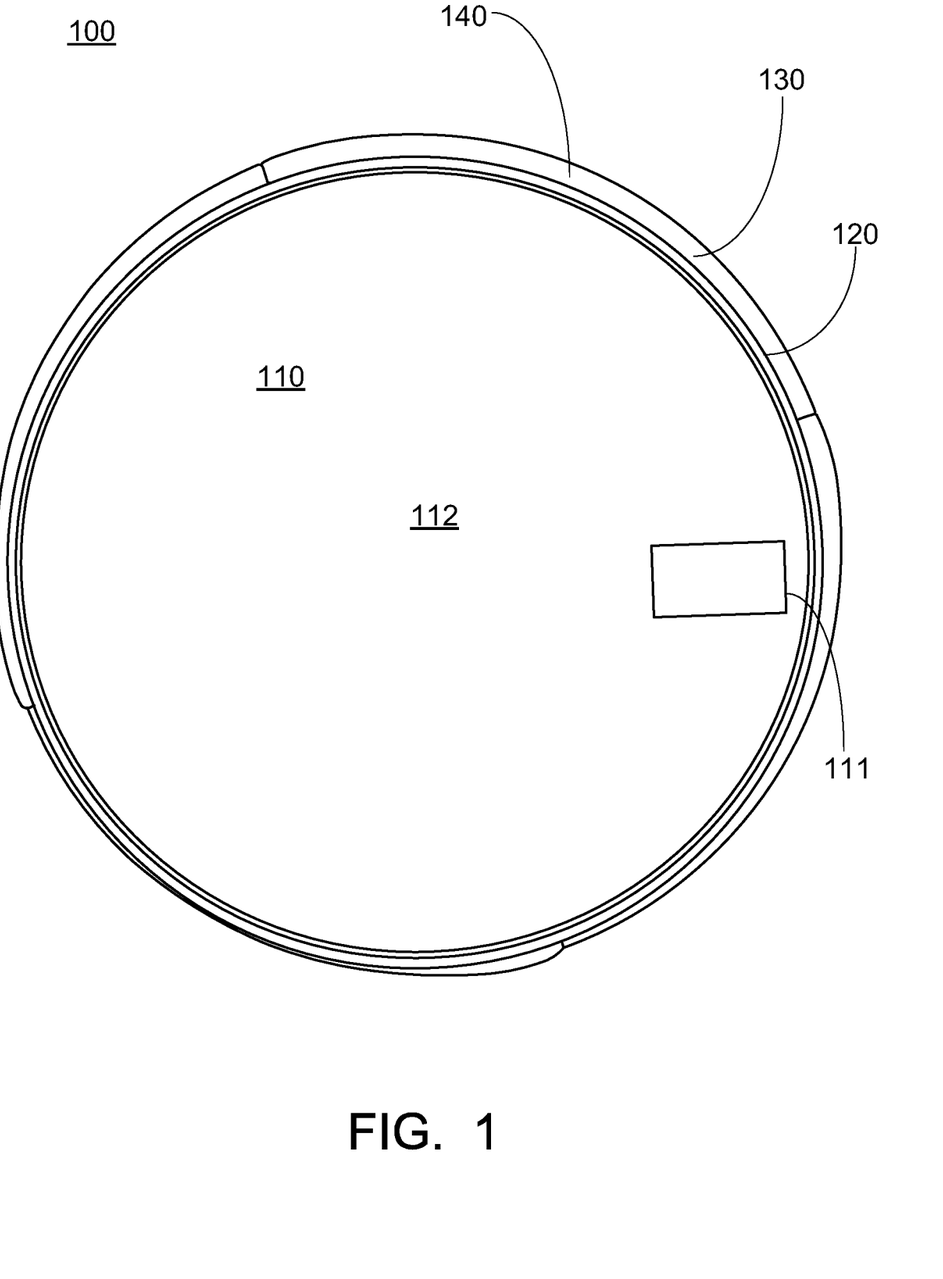
FIG. 1 is a bottom view of a dish in accordance with some embodiments of the present disclosure.
Figure 2:
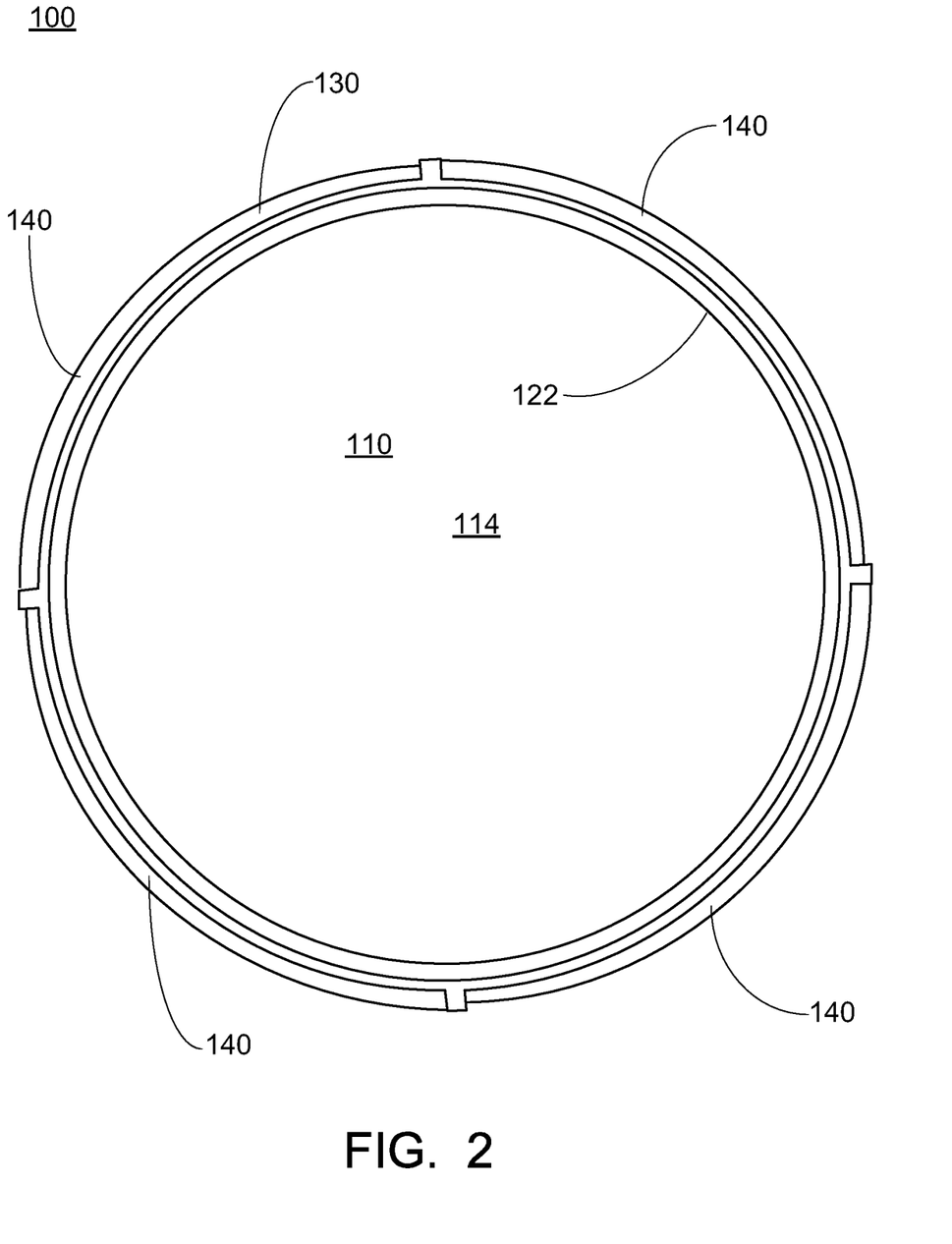
FIG. 2 is a top view of the dish of FIG. 1.
Figure 3:
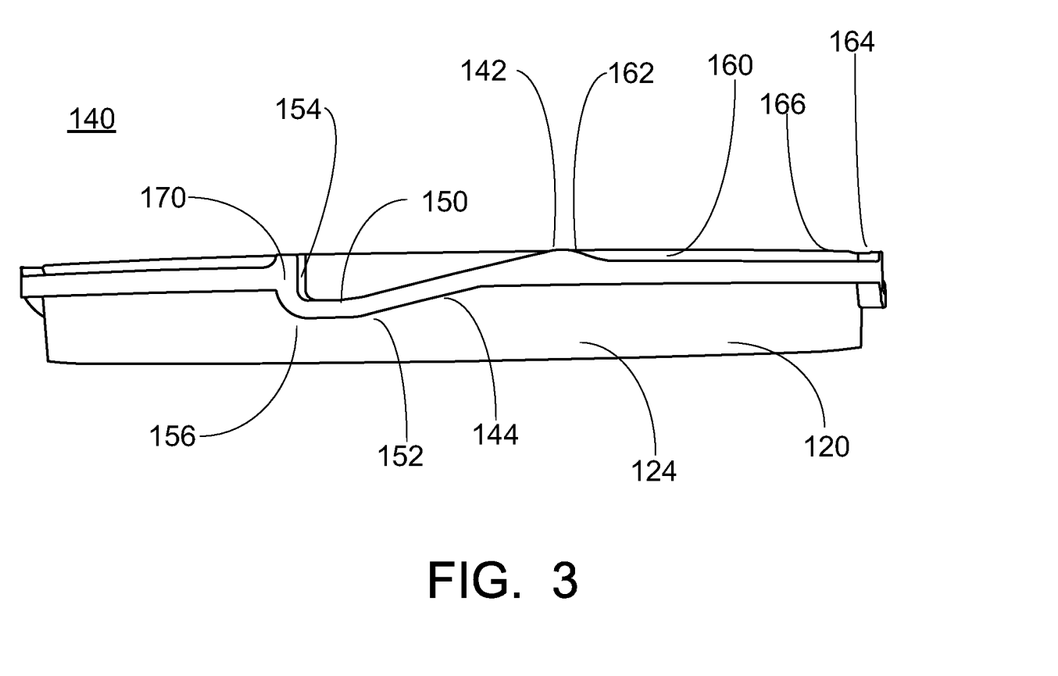
FIG. 3 is a side view of the dish of FIG. 1.
Figure 4:
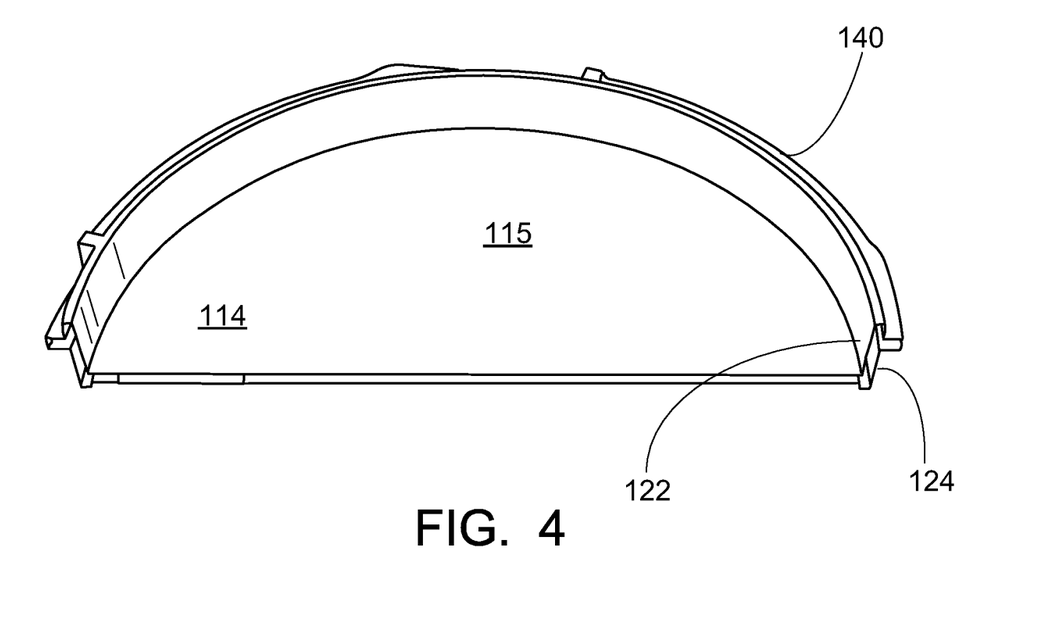
FIG. 4 is a cross-sectional view of the dish of FIG. 1.

FIGS. 1-4 illustrate a culture dish 100, which is one component of the culture apparatuses of the present disclosure. FIG. 1 is a bottom view of the dish. FIG. 2 is a top view of the dish. FIG. 3 is a side view of the dish. FIG. 4 is a cross-sectional view of the dish.

The dish 100 includes a planar base 110 and a sidewall 120 extending upwards therefrom. The planar base 110 includes a bottom surface 112 and a top surface 114. The sidewall 120 includes an inner surface 122 and an outer surface 124. An optional isomark 111 is shown, which provides a reference point on the dish. Together, the planar base and the sidewall define a cavity 115. A culture medium (not shown) may be poured and formed within the cavity.

A track 130 extends outwards from the outer surface 124 of the sidewall. The track runs around the circumference of the sidewall of the dish. The track 130 comprises at least one track portion 140. As best seen in FIG. 2, the dish is illustrated here with four track portions 140. However, any desired other number of track portions may be present, for example, two, three, four, five, or six track portions.

Referring now to FIG. 3, each track portion 140 includes a lower landing 150, a ramp 144, and an upper landing 160. The lower landing 150 is lower than the upper landing 160, or put another way is closer to the planar base 110. The lower landing 150 has a terminal end 156 and a ramp end 152. A stop 154 is present at the terminal end 156. The upper landing also has a terminal end 166 and a ramp end 162. A stop 164 is present at the terminal end 166.

The ramp 144 extends at an angle from the lower landing 150 to the upper landing 160. The ramp 144 extends upwards from the ramp end 152 of the lower landing to the ramp end 162 of the upper landing. If desired, a bump 142 may be present at the between the ramp 144 and the upper landing 160. Put another way, the bump is located at the ramp end 162 of the upper landing. The bump can act as a stop surface as well.

As best seen in FIG. 3, the stop 154 of the lower landing of one track portion and the stop 164 of the upper landing of an adjacent track portion can be provided by a common wall 170.

Figure 5:
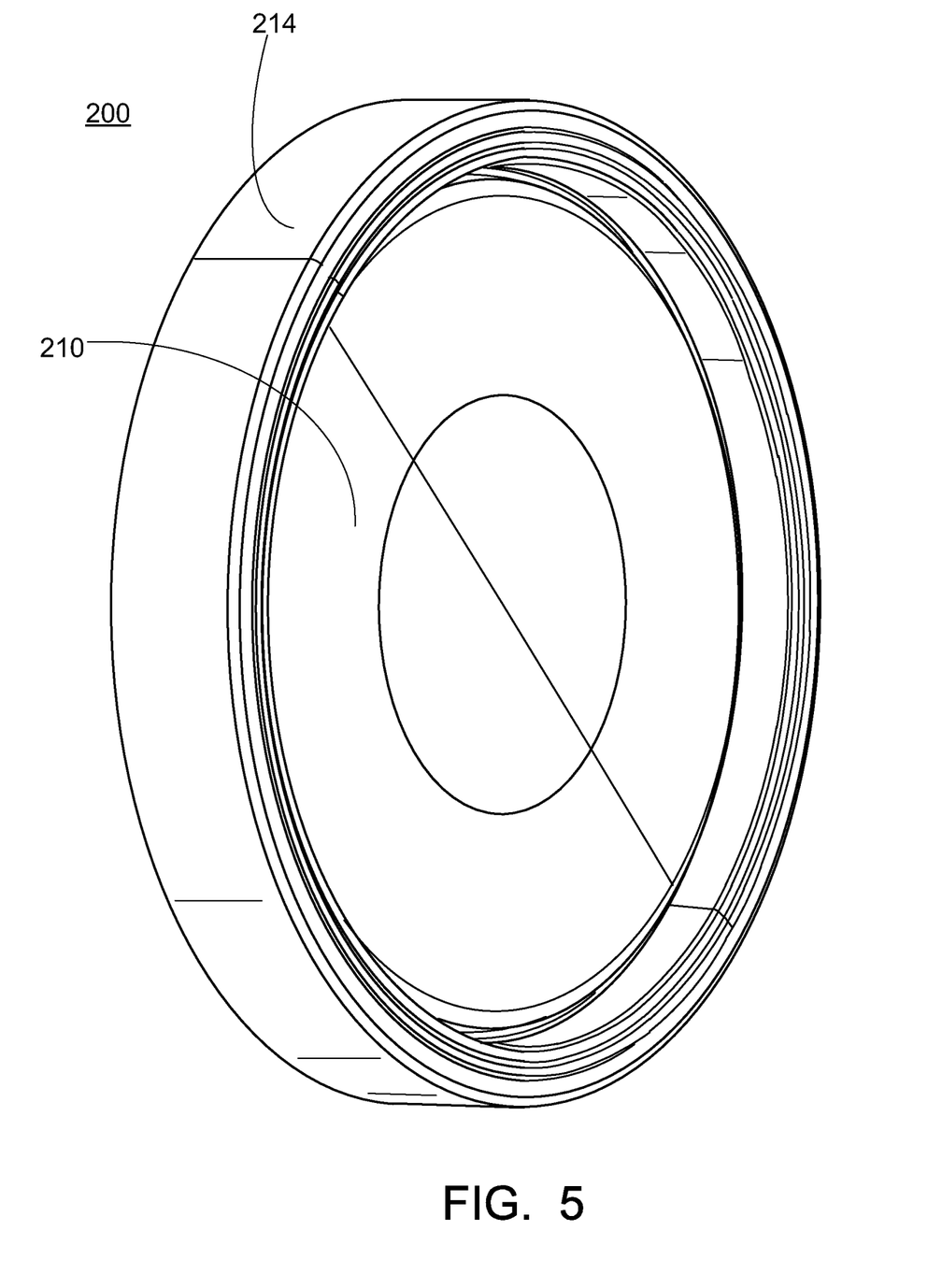
FIG. 5 is a top perspective view of a lid in accordance with some embodiments of the present disclosure.
Figure 6:
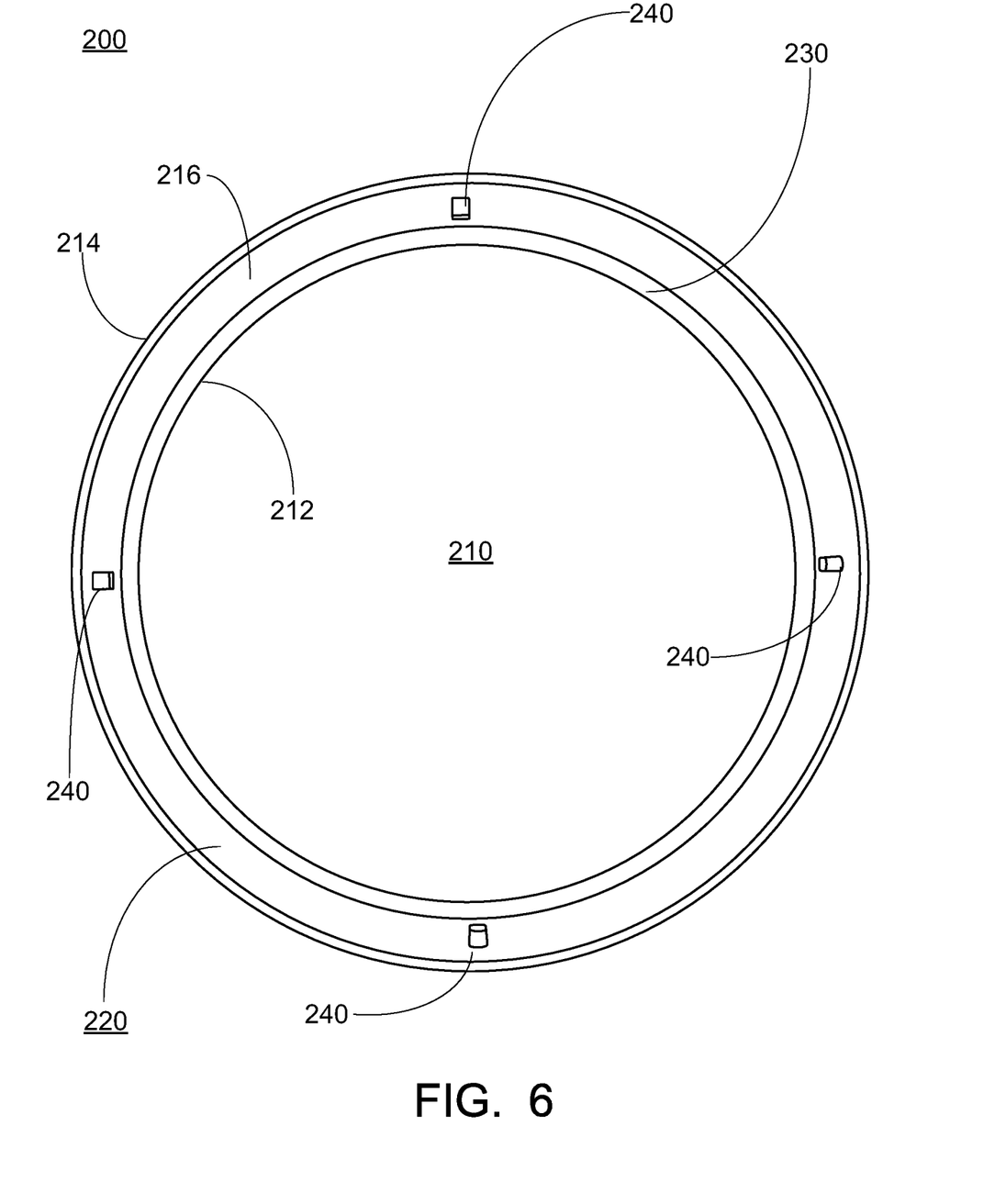
FIG. 6 is a bottom view of the lid of FIG. 5.
Figure 7:
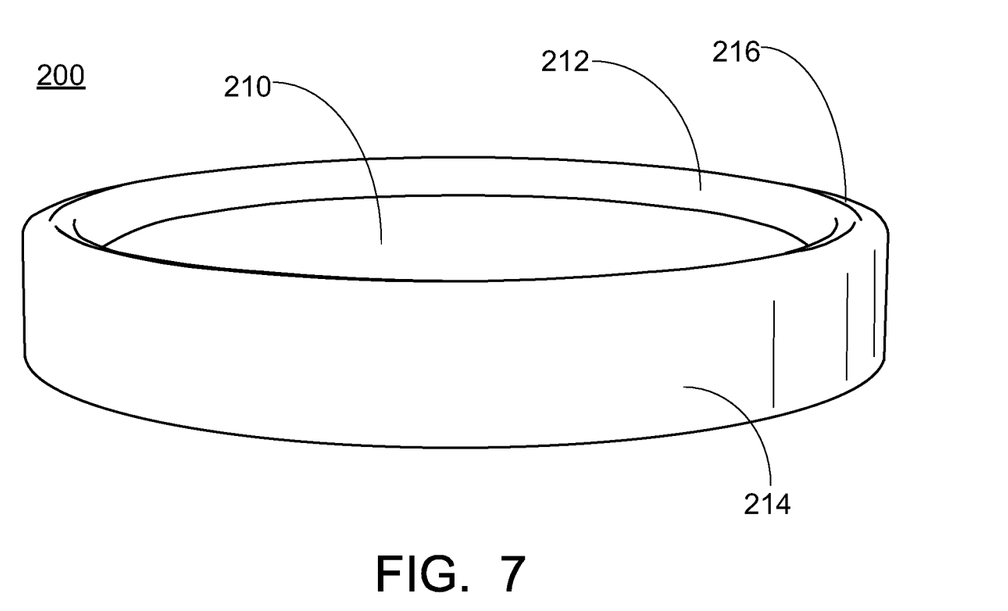
FIG. 7 is a side view of the lid of FIG. 5.
Figure 8:
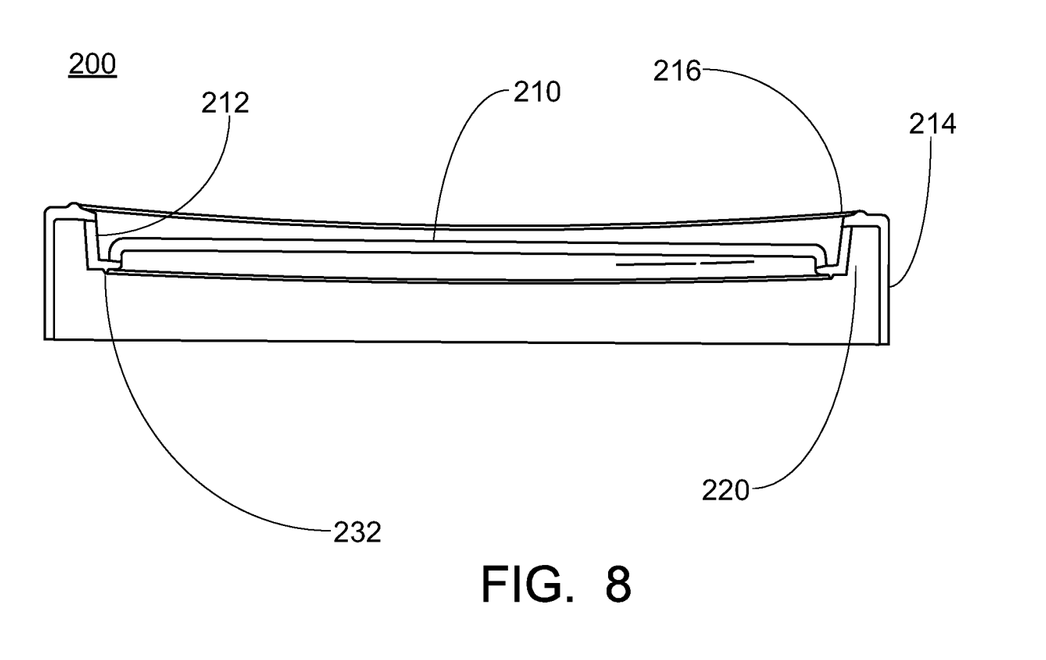
FIG. 8 is a cross-sectional view of the lid of FIG. 5.

FIGS. 5-8 illustrate the lid 200, which is the other component of the culture apparatuses of the present disclosure. FIG. 5 is a top perspective view of the lid. FIG. 6 is a bottom view of the lid. FIG. 7 is a side view of the lid. FIG. 8 is a cross-sectional view of the lid.

The lid 200 is sized to fit or conform over the dish 100. The lid includes a central horizontal wall 210, an inner vertical sidewall 212, an outer vertical sidewall 214, a top wall 216, and a seal ring 230. The outer sidewall is taller than the inner sidewall. The inner sidewall 212 and the outer sidewall 214 are joined together at one end by the top wall 216, which is generally horizontal. Together, these three walls form a downward-facing recess 220. When the lid is assembled with the dish 100, the sidewall 120 of the dish is received in the recess 220 of the lid. The recess can vary in width and height, depending upon the overall size and configuration of the dish and lid.

The central horizontal wall 210 curves downward along its circumference, and the seal ring 230 projects outwardly from the central horizontal wall to the inner sidewall 212. The seal ring is circumferentially continuous and has a planar seal face 232. The seal ring will cooperate with the cell culture media in the dish to define a sealed headspace which can contain an anaerobic environment, as will be discussed in greater detail herein.

Referring now to FIG. 6, the lid 200 also includes at least one key 240, which extends downward from the top wall 216. The key 240 is located within the recess 220. As illustrated here, there are four keys spaced evenly about the circumference of the lid. The keys are spaced apart from the inner sidewall 212, and can be proximate the outer sidewall 214. The keys also have a height.

Figure 9:
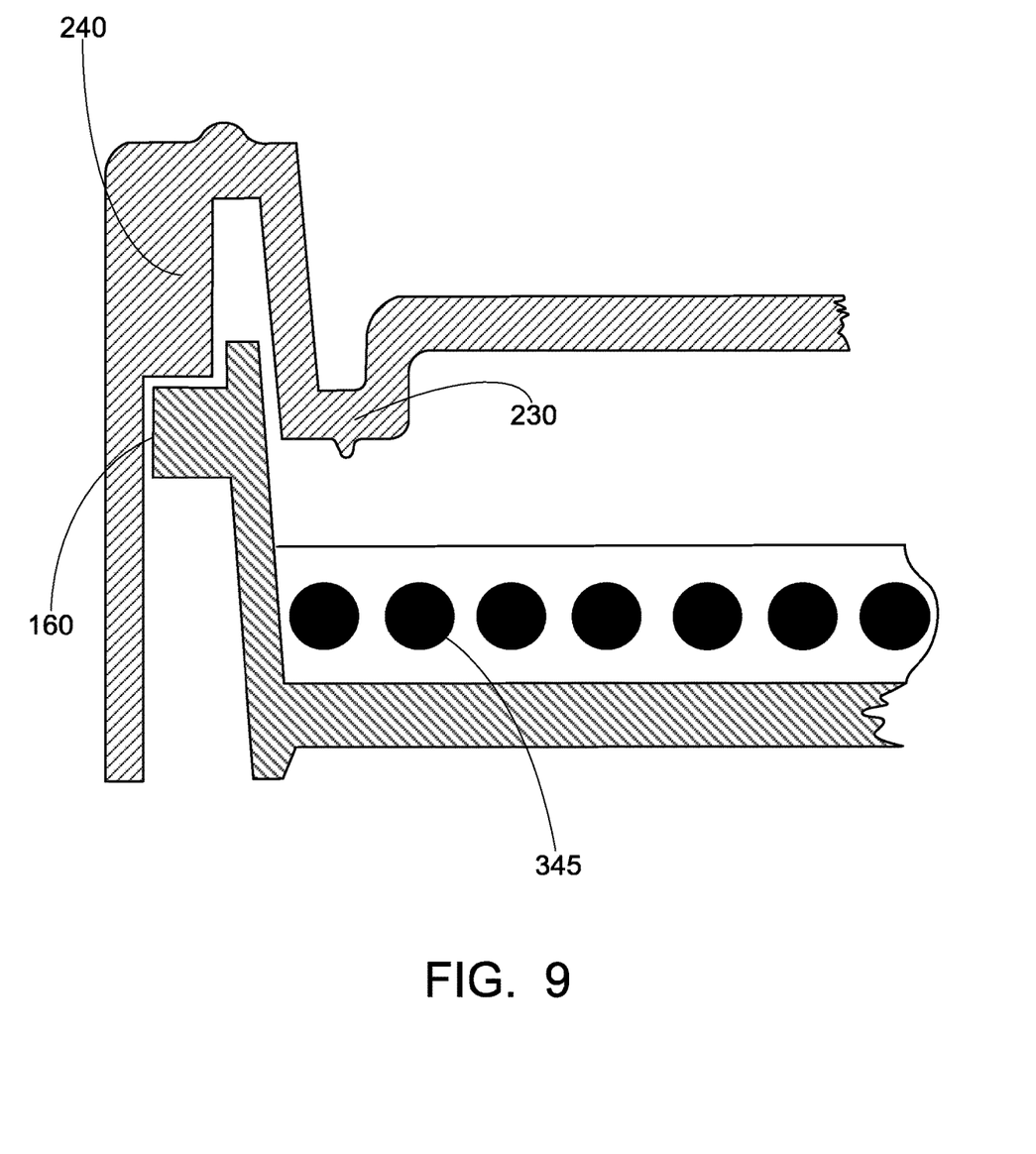
FIG. 9 is a cross-sectional view showing the dish and the lid in an open position.

The combination of the dish and the lid is referred to herein as a plate or culture system. When the lid 200 is placed upon the dish 100, the dish sidewall 120 enters the lid recess 220, and each key 240 rests upon a track portion 140. As seen in FIG. 9, when the keys 240 rest on the upper landing 160, the lid 200 is suspended above the dish such that the seal ring 230 does not contact the surface of the cell culture medium 345. This position may be referred to as an unsealed or open position.

Figure 10:
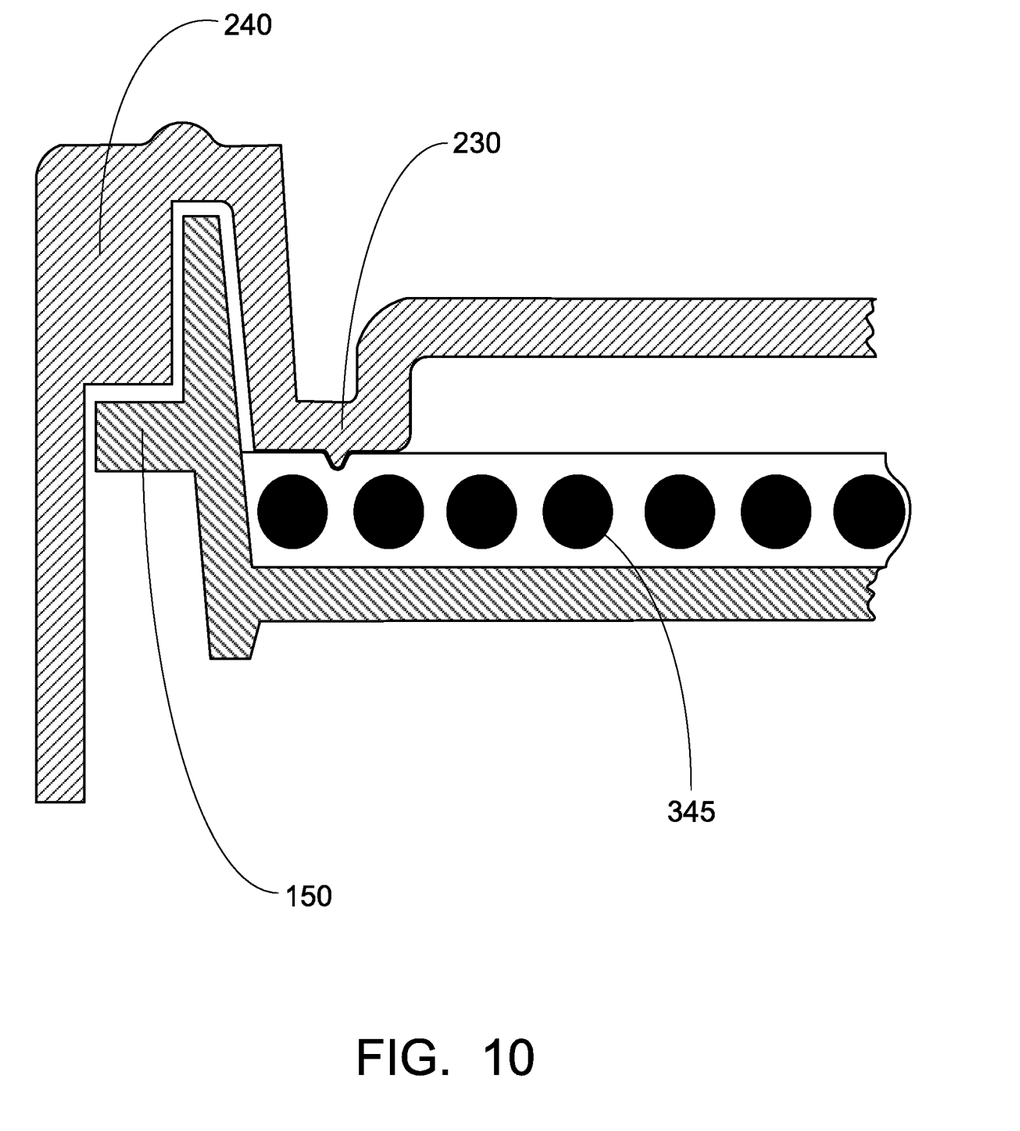
FIG. 10 is a cross-sectional view showing the dish and the lid in a closed position.

As the lid 200 is rotated clockwise relative to the dish 100, the keys travel over the bump 142 and down the ramp 144 to the lower landing 150 of the track portion, such that the lid falls relative to the base 110 of the dish. As seen in FIG. 10, this results in the seal ring 230 contacting the surface of the cell culture medium 345, resulting in a sealed headspace within the plate. This position may be referred to as a sealed or closed position.

When the lid 200 is rotated counter-clockwise relative to the dish, the lid travels from the lower landing 150 up the ramp 144 to the upper landing 160, such that the lid rises relative to the base 110 of the dish. This unseals the lid from the dish, permitting access to the microorganisms on the surface of the cell culture medium.

The upper landing 160 and the lower landing 150 of the track portion 140 are separated by a height, which should be greater than the height of the key. The height of the key should be greater than the distance between the upper landing 160 and the rim of the sidewall 120 of the dish. As a result, (A) the seal ring does not contact the culture media surface when the key engages the upper landing of the track portion; and (B) the seal ring contacts the culture media surface when the key engages the lower landing of the track portion.

The rotating action used to open and close the plate is a smooth operation, protecting the surface of the cell culture medium and not requiring the lid to be distorted (through squeezing) in order to be opened. It is noted that the opening rotation can be in either circumferential direction (clockwise or counter-clockwise) and the closing rotation direction would be in the reverse direction.

This ease of use is useful in reducing accumulation of moisture within the enclosed headspace when the cell culture medium is poured. The plate can be placed in the open position (keys on the upper landing) and then placed in a sealed bag to reduce contamination from the ambient environment. Moisture inside the plate can escape into the bag and be absorbed by a dessicant. The surface of the cell culture medium remains dry. This plate can also be used with auto-streakers that are used to automate the processing of plates with specimens. The lid can be removed from the dish using a suction cup and rotation, and then be placed and sealed again in the same fashion.

Other aspects of the dish and lid are now discussed. These aspects can be used in any combination, as desired.

The dish 100 can be of any convenient dimension, and is usually circular so that this dimension is referenced as a diameter. Typically, the diameter of the dish (as measured at the planar base) is about eight (8.0) to fifteen (15.0) cm. The depth of the dish, defined by the height of the sidewall 120 as it extends upwardly from the base, can vary and is generally about 0.8 to 1.8 cm. The base of the dish can also include dividers, grid markings, or other indicia to enhance differential diagnostics of microorganisms.

The lid 200 can be of any convenient diameter so long as it is compatible with the dish 100. Typically, the lid is approximately nine (9.0) cm to sixteen (16.0) cm in diameter. The seal ring 230 can be of any desired diameter and is generally about seven (7.0) cm to fourteen (14.0) cm in diameter and is centrally positioned relative to the outer sidewall 214 of the lid. The overall radial dimension of the seal ring can vary, with a preferred radial dimension being about two-tenths (0.2) cm to one-half (0.5) cm.

The height of the outer sidewall of the lid should be great enough to keep the planar seal face of the seal ring from contacting the cell culture medium surface. This allows a freshly poured plate with molten agar, to cool and solidify before the media surface of the dish bottom can rest on the seal ring in the dish lid when the assembled plate is inverted. This feature also provides a means for producing finished plates in a continuous manner by mechanized means on a conveyor belt for large scale commercial production while maintaining aseptic conditions.

The inner surface 122 of the dish sidewall may include a lip. The optional lip can act as a guide for indicating the fill level of the cell culture medium. The base and sidewall are shown as a one-piece construction such as a molded arrangement, although other equivalent configurations can be used without departing from the scope of the present disclosure.

If desired, strengthening ribs may be spaced along the outer surface of the outer sidewall 214 of the lid. The ribs are preferably equally spaced about the circumference of the lid and protrude radially outward from the outer surface of the outer sidewall. The ribs provide additional rigidity and strength to the lid, which is particularly helpful when the plates are stacked in either the upright or inverted positions.

In addition, in certain embodiments of the disclosure, a raised area, dome or cavity is present in the lid. Specifically, a dome may project outward from the central horizontal wall of the lid. This dome is designed to contain an anaerobic gas ($CO_2$, etc.) generating pad or element or an indicator strip. The dome may be comprised essentially of a dome side wall and a dome top wall. The dome may have a circular cross-section. In other embodiments, the cross-section of the dome is not circular.

In some embodiments, the base of the dish contains an indicator ring. The area or annulus between the indicator ring on the base and the sidewall identifies the area on the media surface that the seal ring will occupy when the assembled plate is inverted. This area is not to be used for culturing microorganisms. Microbes present in this area will swarm around the seal ring when the lid is placed in contact with the culture media.

The assembled culture plate may be designed so they can be stacked one on top of another. A dish of one assembled plate may be nestled between two lids in the upright positions. In this regard, each lid may have a stacking ring extending upward from the upper edge of the dish lid. While the diameter of the stacking ring can vary, it is generally about one-half (0.5) mm to one (1.0) mm less than the overall peripheral diameter of the dish cover. This provides an outer radial ledge upon which the bottom edge of the sidewall of an adjacent lid rests when placed either in an upright or inverted position. The projection of the stacking ring is preferably about one-half (0.5) mm to one and one-half (1.5) mm in height. The stacking ring prevents an adjacent lid from sliding laterally and upsetting the stacked arrangement.

Similarly, the stacking ring on the lid radially contains or nests an adjacent dish when stacking is desired in an upright position. The stacking ring defines a radial inner ledge to impede slide-out of the enjoining dish bottom. The stacking ring is preferably one-half (0.5) mm to (1.5) mm in width.

A variant of the dish contains one or more pores in the planar base for the purpose of controlling moisture inside the headspace. The size of the pores can vary, but is usually about one-tenth (0.1) cm to three-tenths (0.3) cm in diameter. The number of pores can vary from one (1) to eighty (80) or more and their location can be grouped or evenly spaced. The pores may be covered with an adhesive film such as Mylar which retards the passage of oxygen and can be sterilized in place when the dish is sterilized. This film can be removed after the dish is filled and before it is incubated. The pores provide a means to reduce the water content of the media during incubation in a controlled manner. This reduces the condensate that forms inside the assembled plate. Any oxygen infiltrating into the assembled culture dish through these pores must pass through the media to get to the media surface where the microbes are planted. The media may contain the biocatalytic oxygen reducing agent and optionally one or more substrates that removes the oxygen before it can reach the surface by this route.

The culture dish may be designed to be easily manufactured by known injection molding techniques. The dish lid and dish bottom have no features that prevent them from being ejected from a mold. The materials of construction can vary but are preferably polystyrene, polycarbonate, or polystyrene-acrylonitrile. These are clear thermoplastics that are inexpensive, easy to mold, sterilizable by ethylene oxide or radiation, resilient to handling and resistant to chemical substances used in microbiological media. Styrene-acrylonitrile has the lowest oxygen permeability of the three thermoplastics mentioned. All of the parts are preferably transparent to permit observation of the anaerobic culturing process. However, pigments or dyes may be added to the polymeric materials in order to produce different shades or colors. Further, as it is understood by those skilled in the art, ultra-violet light absorbers and other additives can be added to produce culture dishes having the properties desired by the end user.

In use, when the dish is filled with solidified cell culture media and the assembled plate is inverted, the solidified media surface will come into contact with the seal ring of the lid, forming a media-ring seal along the planar seal face. In this inverted configuration of the plate, an oxygen reducing agent present in the media may remove all of the oxygen that is trapped in the headspace of the enclosed chamber formed between the surface of the solidified media and the inner surface of the lid. This results in an internal anaerobic environment for the growth of anaerobe microorganisms.

The cell culture media can contain biocatalytic oxygen reducing agents. In particular, some known oxygen reducing agents include oxygen scavenging membrane fragments. The membrane fragments, which contain an electron transport system that reduces oxygen to water, may be obtained from various sources. It is known that a great number of bacteria have cytoplasmic membranes which contain the electron transport system that effectively reduces oxygen to water if a suitable hydrogen donor is present in the medium. Some suitable bacterial sources include *Escherichia coli, Salmonella typhimurium, Gluconobacter oxydans, Pseudomonas aeruginosa*, and *Acetobacter*. These bacterial membranes have been highly effective in removing oxygen from media and other aqueous and semi-solid environments.

The same oxygen reducing effects produced by the cell membrane fragments from the bacterial sources indicated above can also be obtained by the use of oxygen reducing membranes from, for example, the mitochondrial organelles of a large number of higher non-bacterial organisms. More particularly, a great number of fungi, yeasts, plants, and animals have mitochondria that reduce oxygen to water if a suitable hydrogen donor is present in the medium. Some of the sources of oxygen reducing membranes from these mitochondria are: beef heart muscle, potato tuber, spinach, *Saccharomyces, Neurospora, Aspergillus, Euglena*, and *Chlamydomonas*.

A hydrogen donating substance (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts. The hydrogen donating substance may be present in the composition in the amount of about 1 wt % to about 5 wt %.

The biocatalytic oxygen reducing agents suitable for use in the present disclosure are non-toxic to microorganisms. Being catalysts, they are dynamic and highly efficient at reducing the oxygen in the trapped headspace in the specially designed culture dish. The biocatalytic oxygen reducing agents use substrates that are commonly found in microbiological media and that are natural to microorganisms to effect this reaction. The products produced from this reaction are also natural and non-toxic to microorganisms. The use of the biocatalytic oxygen reducing agents makes possible the opening and closing of this dish several times and the agents continue to reduce the oxygen trapped in the headspace after each occurrence.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An apparatus for cultivating anaerobe microorganisms, comprising:
 a dish comprising a base, a sidewall extending upwards from the base to define a cavity, and a track extending outwards from an outer surface of the sidewall;
 wherein the track comprises at least one track portion, the at least one track portion including a lower landing with a stop at a terminal end, a ramp extending from the lower landing to an upper landing, and a stop at a terminal end of the upper landing; and
 a lid comprising a central horizontal wall, a downward-facing recess, and at least one key extending downwards from a top wall of the recess;
 wherein the at least one key cooperates with the at least one track portion so that (A) the lid rises relative to the base of the dish when the lid is rotated in a first circumferential direction, and (B) the lid falls relative to the base of the dish when the lid is rotated in an opposite circumferential direction, and wherein, during rotation of the lid, the at least one key is configured to engage with the at least one track portion such that the at least one key travels along and maintains in contact with the lower landing, ramp and the upper landing.

2. The apparatus of claim 1, wherein the at least one track portion further comprises a bump between the ramp and the upper landing.

3. The apparatus of claim 1, wherein the at least one track includes a total of four track portions evenly spaced about a circumference of the dish, and the at least one key of the lid includes a total of four keys evenly spaced about a circumference of the lid.

4. The apparatus of claim 3, wherein the lower landing stop and the upper landing stop are provided by a common wall shared by adjacent track portions.

5. The apparatus of claim 1, wherein the central horizontal wall of the lid is joined to the downward-facing recess by a seal ring; and
 wherein the downward-facing recess is formed by an outer sidewall and an inner sidewall joined together at one end by the top wall.

6. The apparatus of claim 5, wherein the upper landing and the lower landing of the at least one track portion are at different elevations along the sidewall such that when an associated culture media having a surface is formed in the dish, (A) the seal ring does not contact the culture media surface when the at least one key engages the upper landing of the at least one track portion; and (B) the seal ring contacts the culture media surface when the at least one key engages the lower landing of the at least one track portion.

7. The apparatus of claim 5, wherein the outer sidewall is taller than the inner sidewall.

8. The apparatus of claim 5, wherein the lid further comprises strengthening ribs spaced about a circumference of the lid and extending radially outward from the outer sidewall.

9. The apparatus of claim 1, wherein the lid further comprises a stacking ring extending upwards from an upper edge of the lid.

10. The apparatus of claim 1, wherein the dish further comprises a lip on an inner surface of the sidewall.

11. The apparatus of claim 1, wherein the base of the dish includes pores.

12. A method of cultivating and enumerating anaerobes, microaerophiles, or facultatively anaerobe microorganisms, comprising:
 providing a culture apparatus comprising a dish and a lid;
  wherein the dish comprises a base, a sidewall extending upwards from the base to define a cavity, and a track extending outwards from an outer surface of the sidewall; and
  wherein the track comprises at least one track portion, the track portion including a lower landing with a stop at a terminal end, a ramp extending from the lower landing to an upper landing, and a stop at a terminal end of the upper landing; and
  wherein the lid comprises a central horizontal wall, a downward-facing recess, and at least one key extending downwards from a top wall of the recess;
  wherein the at least one key cooperates with the at least one track portion so that (A) the lid rises relative to the base of the dish when the lid is rotated in a first circumferential direction, and (B) the lid falls relative to the base of the dish when the lid is rotated in an opposite circumferential direction, and wherein, during rotation of the lid, the at least one key is configured to engage with the at least one track portion such that the at least one key travels along and maintains in contact with the lower landing, ramp and the upper landing;
 placing a solidified culture medium in the dish; and
 covering the dish containing the solidified culture medium with the lid such that the at least one key engages the lower landing of the at least one track portion, thereby forming a sealed headspace between the culture medium and the lid.

13. The method of claim 12, further comprising:
 unsealing the culture dish by circumferentially rotating the lid relative to the dish.

14. The method of claim 12, wherein the solidified culture medium comprises an oxygen reducing agent that removes oxygen from the headspace and the culture medium.

15. The method of claim 12, wherein the at least one track portion further comprises a bump between the ramp and the upper landing.

16. The method of claim 12, wherein the at least one track includes a total of four track portions evenly spaced about a circumference of the dish, and the at least one key of the lid includes a total of four keys evenly spaced about a circumference of the lid.

17. The method of claim 16, wherein the lower landing stop and the upper landing stop are provided by a common wall shared by adjacent track portions.

18. The method of claim 12, wherein the central horizontal wall of the dish is joined to the downward-facing recess by a seal ring; and
 wherein the downward-facing recess is formed by an outer sidewall and an inner sidewall joined together at one end by the top wall.

19. The method of claim 18, wherein the upper landing and the lower landing of the at least one track portion are at different elevations along the sidewall such that when an associated culture media having a surface is formed in the dish, (A) the seal ring does not contact the culture media surface when the at least one key engages the upper landing of the at least one track portion; and (B) the seal ring contacts the culture media surface when the at least one key engages the lower landing of the at least one track portion.

20. The method of claim 19, wherein the outer sidewall is taller than the inner sidewall; or wherein the lid further comprises strengthening ribs spaced about a circumference of the lid and extending radially outward from the outer sidewall; or wherein the lid further comprises a stacking ring extending upwards from an upper edge of the lid; or wherein the dish further comprises a lip on an inner surface of the sidewall, and the surface of the solidified culture medium is at or below the lip; or wherein the base of the dish includes pores.

* * * * *